United States Patent [19]
Gast

[11] Patent Number: 5,858,405
[45] Date of Patent: *Jan. 12, 1999

[54] ORAL CONTRACEPTIVE

[75] Inventor: Michael J. Gast, Phoenixville, Pa.

[73] Assignee: American Home Products Corporation, Madison, N.J.

[ * ] Notice: The term of this patent shall not extend beyond the expiration date of Pat. No. 5,747,480.

[21] Appl. No.: 887,162

[22] Filed: Jul. 2, 1997

Related U.S. Application Data

[60] Provisional application No. 60/022,624 Jul. 26, 1996.
[51] Int. Cl.⁶ .............................. A61K 9/20; A61K 31/56
[52] U.S. Cl. ......................... 424/464; 514/170; 514/841; 514/843
[58] Field of Search ............................ 424/464; 514/170, 514/841, 843

[56] References Cited

U.S. PATENT DOCUMENTS

| | | | |
|---|---|---|---|
| 3,957,982 | 5/1976 | Lachnit-Fixson et al. | 424/238 |
| 3,969,502 | 7/1976 | Lachnit-Fixson | 424/239 |
| 4,248,790 | 2/1981 | Ponsold et al. | 260/397.4 |
| 4,273,771 | 6/1981 | Coussediere | 424/242 |
| 4,390,531 | 6/1983 | Edgren | 424/239 |
| 4,530,839 | 7/1985 | Pasquale | 514/171 |
| 4,621,079 | 11/1986 | Lachnit-Fixson et al. | 514/170 |
| 4,628,051 | 12/1986 | Pasquale | 514/170 |
| 4,921,843 | 5/1990 | Pasquale | 514/170 |
| 4,962,098 | 10/1990 | Boissonneault | 514/170 |
| 5,262,408 | 11/1993 | Bergink | 514/182 |
| 5,280,023 | 1/1994 | Ehrlich et al. | 514/177 |
| 5,418,228 | 5/1995 | Bennink | 514/182 |
| 5,583,129 | 12/1996 | Spona et al. | 514/178 |
| 5,747,480 | 5/1998 | Gast | 514/179 |

FOREIGN PATENT DOCUMENTS

| | | |
|---|---|---|
| 0253607 | 1/1988 | European Pat. Off. . |
| 0628312 | 12/1994 | European Pat. Off. . |
| 0696454 | 2/1996 | European Pat. Off. . |
| 4104385 | 8/1992 | Germany . |
| 4313926 | 11/1994 | Germany . |
| 9517194 | 6/1995 | WIPO . |
| 9526730 | 10/1995 | WIPO . |

OTHER PUBLICATIONS

Sartoretto et al., Clinical evaluation of a low dosage estrogen–progesterone association (100μg of d–norgestrel and 20μg ethinyl [sic] estradiol), Clinica e Terapeutica (1974) 3:399–404.

Primary Examiner—Thurman K. Page
Assistant Examiner—James M. Spear
Attorney, Agent, or Firm—Arnold S. Milowsky

[57] ABSTRACT

This invention provides a bridged triphasic combination progestin/estrogen oral contraceptive regimen comprising the administration of a contraceptive progestin/estrogen combination for 23–25 days consecutive days beginning on the first day of menses, followed by the administration of an estrogen for 3–5 days following the administration of the estrogen/progestin combination, so that the total period of administration is 28 days per 28 day cycle. Particularly preferred progestins of this invention are trimegestone, dienogest, and drospirenone.

20 Claims, No Drawings

ORAL CONTRACEPTIVE

BACKGROUND OF THE INVENTION

This application claims the benefit of U.S. Provisional Application No. 60/022,624, filed Jul. 26, 1996.

The vast majority of oral contraceptives consist of a combination of a progestin and estrogen that are administered concurrently for 21 days followed either by a 7 day pill free interval or by the administration of a placebo for 7 days in each 28 day cycle. The most important aspects of a successful oral contraceptive product are effective contraception, good cycle control (absence of spotting and breakthrough bleeding and occurrence of withdrawal bleeding), and minimal side effects. Combination oral contraceptives have traditionally acted by suppression of gonadotropins. In addition, it appears that the progestin component is primarily responsible for contraceptive efficacy through inhibition of ovulation, and other peripheral effects which include changes in the cervical mucus (which increase the difficulty of sperm entry into the uterus) and the endometrium (which reduce the likelihood of implantation). The estrogenic component intensifies the anovulatory effect of the progestin, and is also important for maintaining cycle control.

Since the introduction of oral contraceptives (OCs) over a quarter-century ago, research has been directed toward developing preparations that minimize the potential for side effects while maintaining efficacy and normal menstrual patterns. The first-generation OCs contained more progestin and estrogen than was necessary to prevent conception. Adverse hemostatic and metabolic changes, clinical problems, and side effects were associated with these high-dose preparations. In 1978, the World Health Organization (WHO) recommended that the focus of OC research should be the development of products containing the lowest possible dose levels of estrogen and progestin.

The first reductions in steroid content in a combination pill were focused on estrogen because it, rather than progestin, was thought to be related to the most serious side effects. Reduction in progestin content followed, as evidence mounted that lowering progestin intake might lower the risk of cardiovascular complications such as stroke and ischemic heart disease. [Kay CR, Am J Obstet Gynecol 142:762 (1982)]. However, this evidence was not as clear as that implicating estrogen in thromboembolic disorders. [Inman WHW, Br Med J 2:203 (1970); Stolley PD, Am J Epidemiol 102:197 (1975)]. The need for a balance between estrogens and progestins to minimize adverse effects on carbohydrate metabolism and on lipid and lipoprotein levels was also recognized. [Bradley DD, N Engl J Med 299:17 (1978); Wynn V, Lancet 1:1045 (1979)]. Researchers then found that the synergistic action between progestin and estrogen in a balanced ratio successfully inhibited ovulation at low levels of both components.

Research into low-dose progestins was advanced significantly by the development of norgestrel (Ng) and levonorgestrel (LNg). Levonorgestrel is the biologically active moiety of racemic norgestrel. It is strongly progestational, has no inherent estrogenic activity, is antiestrogenic, and possesses good biologic activity. The contraceptive effects of levonorgestrel are manifested throughout the hypothalamic-pituitary-gonadal-target organ axis.

Ethinyl estradiol (EE) is the estrogen most frequently used in combination OCs. In attempts to fulfill the WHO objective, the dosage of EE in marketed OC formulations has been steadily reduced from that found in earlier OCs. Thromboembolic mortality decreased when the amount of synthetic estrogen in OC formulations was reduced from 100 µg to 50 µg. Subsequently, a significant reduction in fatal myocardial infarctions was reported for women using OCs with 30 µg of EE rather than 50 µg of EE. [Meade TW, Br Med J 280:1157 (1980)].

In keeping with the goal of reducing the total steroidal dosage, while maintaining contraceptive efficacy, good cycle control, and minimizing side effects, numerous regimens have been developed in which the progestin/estrogen combination is administered either as a fixed dosage combination (monophasic) or as biphasic or triphasic regimens in which the dosage of the combination is varied either once or twice throughout the menstrual cycle. In these regimens, the progestin/estrogen combination is typically administered for 21 days followed by either a 7-day pill free period or the administration of a non-contraceptive placebo (or iron supplement) for 7 days. In these regimens, 3-ketodesogestrel (3-KDSG), desogestrel (DSG), levonorgestrel (LNg), gestodene (GTD), norgestrel (NG), and norethindrone (NE) are typically used as the progestin while ethinyl estradiol (EE); 17β-estradiol, and mestranol are typically the estrogenic components. Other progestins less frequently used include drospirenone (DRSP) and dienogest (DGST).

An oral contraceptive product containing a combination of 3 mg DGST and 30 µg EE for 21-day administration per cycle is marketed in Germany.

Several examples of attempts at reducing the total steroidal dosage are provided below.

Lachnit (PCT Publication WO 95/26730) discloses bridged regimens consisting of the administration of a combination of a progestin/estrogen combination (50–125 µg LNg and 10–40 µg EE) for the first 23–24 days of the menstrual cycle followed by the administration of an estrogen (2–40 µg EE) for 4–10 days for a total administration of at least 28 days per cycle. The use of 100–300 µg drospirenone and 10–40 µg EE as the 23–24 day progestin/estrogen combination is disclosed. Lachnit also discloses a triphasic plus bridging regimen (4–9 days, 4–9 days, 9–13 days, and 28 days for the three phases and estrogen phase, respectively) in which a combination of 50 µg LNg and 20 µg EE are administered in the first phase, a combination of 75 µg LNg and 25 µg EE are administered in the second phase, a combination of 100 µg LNg and 20 µg EE are administered in the third phase, and 10 µg EE is administered in the estrogen phase. Other progestins disclosed include GTD, DSG, 3-KDSG, DRSP, cyproterone acetate, norgestimate, and norethisterone.

Erlich (German Patent DE 4,104,385 Cl and U.S. Pat. No. 5,280,023) discloses sequential contraceptive regimens consisting of the administration of an estrogen which effects a disturbance of follicle stimulation, followed by the administration of a combination of a progestin/estrogen in a dose at least adequate to inhibit ovulation. The regimen is administered for a total of 28 days per cycle. It is preferred that the estrogen is administered for 5–14 days per cycle and the progestin/estrogen combination is administered for 23–14 days per cycle, so that the total administration is for 28 days per cycle. Specific regimens include (a) 4 mg estradiol for 7 days followed by 21 days of the combination of 1 mg norethisterone acetate and 4 mg estradiol; (b) 2 mg estradiol valerate for 7 days followed by 21 days of the combination of 2 mg chlormadinone acetate and 4 mg estradiol valerate; and (c) 20 µg EE followed by 18 days of the combination of 150 µg LNg and 20 µg EE. Regimen (c) in Erlich provides a total steroidal load of 2.7 mg of LNg and 560 µg EE per 28 day cycle.

Moore (DE 4313926 Al) discloses bridged triphasic regimens consisting of the administration of a combination of 10–50 μg LNg and 5–20 μg EE from days 1–7 of the menstrual cycle; of 50–75 μg LNg and 5–20 μg EE from days 8–14 of the menstrual cycle; of 75–125 μg LNg and 5–20 μg EE from days 15–21 of the menstrual cycle; and 5–20 μg EE from days 22–28 of the menstrual cycle.

Oettel (EP 696,454 A2) discloses a three phase contraceptive regimen in which the first phase consists of the administration for 3–4 days of a composition containing at least one biogenic estrogen; the second phase consists of the administration for 20–22 days of at least one biogenic estrogen and at least one progestin (progesterone, DGST, desogestrel, 3-KDSG, GTD, LNg, norgestimate, notethisterone, norethisterone acetate, dehydrogestrone, chloimadinone acetate, cyproterone acetate, medroxyprogesterone acetate, or megestrol acetate); and the third phase consists of the administration for 3–4 days of a composition containing at least biogenic one estrogen.

Spona (PCT Publication WO 95/17194) discloses contraceptive regimens which consist of the administration of a combination of a progestin (50–75 μg GTD, 75–125 μg LNg, 60–150 μg DSG, 60–150 FIG. 3-KDSG, 100–300 μg DRSP, 100–200 μg cyproterone acetate, 200–300 μg norgestimate, or >350–750 μg norethisterone) and an estrogen (15–20 μg EE or 2–6 μg 17β-estradiol) for 23–24 days per cycle.

Oettel (EP 628,312 Al) discloses combination contraceptive combinations containing the combination of three components: a biogenic estrogen (estradiol, estrone, or estiol), a synthetic estrogen (EE or mestranol), and a progestin (LNg, desogestrel, progesterone, norethisterone acetate, DGST, chlormadinone acetate, gestodene, or cyproterone acetate). In one embodiment, the combination is administered for 21 days followed by the administration of placebo (or pill free) or an estrogen on days 22–28 of the cycle.

Upton (EP Patent Specification 253,607 B 1) teaches the use of low dose progestin/estrogen combinations for combined hormone replacement therapy and contraception in climacteric women. Climacteric women are defined in Upton as premenopausal women around 40 years of age whose hormone levels are waning. The climacteric woman still ovulates (albeit may have irregular ovulation), but she still experiences many of the symptoms of the hypoestrogenic menopausal woman, such as insomnia, hot flushes, and irritability. Upton teaches the administration of a 23–26 day monophasic regimen of progestin/estrogen followed by a pill free or placebo interval of 2–5 days; with 24 days of progestin/estrogen administration followed by a 4-day pill free or placebo administration being preferred. Upton teaches the use of a progestin selected from 25–100 μg LNg, 10–70 μg GTD, 25–100 μg DSG, 25–100 μg 3-KDSG, and 85–350 μg NE used in combination with an estrogen selected from 500–2000 μg 17β-estradiol, 8–30 μg EE, and 15–60 μg mestranol. Based on relative potencies, Upton teaches that a dose of 75 μg LNg is equivalent to 35 μg of GTD, 75 μg of 3-KDSG or DSG, and 250 μg NE and that a dose of 1000 μg of 17β-estradiol is equivalent to a dose of 15 μg EE and 30 μg mestranol. Upton also teaches that NG may be substituted for LNg, but at twice the dose.

Saitoretto (Clinica e Terapeutca 3: 399 (1974)) discloses a monophasic contraceptive regimen consisting of the administration of a combination 100 μg LNg and 20 μg EE for 21 days.

Lachnit-Fixson (U.S. Pat. No. 3,969,502) discloses biphasic progestin/estrogen combination regimens in which a combination of 50–125 μg LNg and 25–35 μg EE are administered for 10–12 days in the first phase and 100–350 μg LNg and 30–50 μg EE are administered for 10–12 days in the second phase. Placebo is administered for 5–7 days following the administration of the contraceptive steroid regimen.

Lachnit-Fixson (U.S. Pat. No. 3,957,982) discloses triphasic 21-day progestin/estrogen regimens in which a combination of 40–90 μg LNg and 20–50 μg EE is administered for 4–6 days in the first phase, 50–125 μg LNg and 30–50 μg EE is administered for 4–6 days in the second phase, and 100–250 μg LNg and 25–50 μg EE is administered for 9–11 days in the third phase. It is preferred that the first, second, and third phases are 6, 5, and 10 days, respectively.

Bennick (U.S. Pat. No. 5,418,228) discloses triphasic regimens which consist of the administration of a combination progestin/estrogen in a 6–8 day phase, a second 6–8 day phase, and a third 6–8 day phase, with it being preferred that the three contraceptive steroid phases be 7 days each. Bennick discloses that the first contraceptive steroid phase consists of a progestin at a daily dosage equivalent to 75–150 μg DSG and an estrogen at a daily dosage equivalent to 20–25 μg EE; the second contraceptive steroid phase consists of a progestin at a daily dosage equivalent to 75–125 μg DSG and an estrogen at a daily dosage equivalent to 20 μg EE; and the third contraceptive steroid phase consists of a progestin at a daily dosage equivalent to 75–100 μg DSG and an estrogen at a daily dosage equivalent to 20 μg EE. Placebo is administered for 7 days following the 21-day contraceptive steroid period. Bennick discloses that the progestin may be 3-KDSG, DSG, LNg, or GTD.

Bergink (U.S. Pat. No. 5,262,408) discloses a 24 day triphasic combination regimen in which the first 7–9 day phase consists of the administration of a progestin at a daily dosage equivalent to 100 μg DSG and an estrogen at a daily dosage equivalent to 25 μg EE, the second 7–9 day phase consists of the administration of a progestin at a daily dosage equivalent to 125 μg DSG and an estrogen at a daily dosage equivalent to 20 μg EE, and the third 7–9 day phase consists of the administration of a progestin at a daily dosage equivalent to 50 μg DSG and an estrogen at a daily dosage equivalent to 20 μg EE. It is preferred that the three phases be 8 days each. Following the 24 day contraceptive steroid administration, a placebo may be administered for 4 days, the 4 day interval may be pill free, or a progestin at a dosage equivalent to 25–35 μg DSG may be administered.

Boissonneault (U.S. Pat. No. 4,962,098) discloses triphasic progestin/estrogen combinations in which the amount of the estrogenic component is increased stepwise over the three phases. Contraceptive steroid combinations are taken for 4–7 days during the first phase (5 days being preferred); for 5–8 days during the second phase (7 days preferred); and for 7–12 days during the third phase (9 days being preferred). Following the administration of 21-days of the contraceptive steroid combination, placebo is taken for 7 days. For all three phases, 0.5–1.5 mg of norethindrone acetate is used in tie progestin, with 1 mg being preferred. 10–30 μg EE is used in the first phase, 20–40 μg in the second, and 30–50 μg in the third phase.

Pasquale (U.S. Pat. No. 4,921,843) discloses combination progestin/estrogen contraceptive regimens which contain 0.5 to 1 mg of progestin and an estrogen having a dose equivalent to 10–40 μg of EE. NE, LNg, D-17β-acetoxy-13β-ethyl-17α-ethinyl-gon-4-en-3-one oxime, and 19-nor-17-hydroxy progesterone ester are disclosed as progestins, with NE being preferred. Specifically disclosed regimens include a uniphasic regimen (2 days of placebo, 5 days of 20 μg EE, and 21 days of a combination of 500 μg NE and 35 μg EE); a uniphasic regimen (2 days of placebo, 5 days of 40 μg EE, and 21 days of a combination of 500 μg NE and 35 μg EE); and a triphasic regimen (2 days of placebo; 5 days of 20–40 μg EE; 7 days of a combination of 500 μg NE and 35 μg EE; 7 days of a combination of 750 μg NE and 35 μg EE; and 7 days of a combination of 1 mg NE and 35 μg EE).

Pasquale (U.S. Pat. No. 4,628,051) discloses triphasic progestin/estrogen combination regimens in which contraceptive steroid is administered for 21 days. Contraceptive steroid combinations are taken for 5–8 days during the first phase (7 days being preferred); for 7–11 days during the second phase (7 days preferred); and for 3–7 days during the third phase (7 days being preferred). In all three phases, an estrogen at a daily dosage equivalent to 20–50 μg EE is administered in combination with a progestin having a daily dosage equivalent to 65–750 μg NE in the first phase, 0.25–1.0 mg NE in the second phase, and 0.35–2.0 mg NE in the third phase. A specific triphasic regimen discloses the administration of 35 μg EE in each of the three 7-day phases in combination with 0.5 mg, 0.75 mg, and 1.0 mg in the first, second, and third phases, respectively. A second specific triphasic regimen discloses the administration of 35 μg EE in each of the three 7-day phases in combination with 50 μg, 75 μg, and 100 μg in the first, second, and third phases, respectively. A third specific triphasic regimen discloses the administration of 35 μg EE in each of the three 7-day phases in combination with 25 μg, 35 μg, and 50 μg in the first, second, and third phases, respectively.

Lachnit-Fixson (U.S. Pat. No. 4,621,079) discloses triphasic 21-day progestin/estrogen combination regimens in which a combination of 40–70 μg GTD and 20–35 μg EE is administered for 4–6 days in the first phase; 50–100 μg GTD and 30–50 μg EE is administered for 4–6 days in the second phase; and 80–120 μg GTD and 20–50 μg EE is administered for 9–11 days in the third phase. Placebo is administered for 7 days following the 21-day contraceptive steroid regimen.

Pasquale (U.S. Pat. No. 4,530,839) discloses triphasic 21-day progestin/estrogen combination regimens in which a dose of 20–50 μg EE is administered in all three phases in combination with a contraceptively effective daily dose of progestin in the first phase, 1.5–2 times that dose of progestin in the second phase, and 2–2.5 times the first phase dose of progestin in the third phase. Each of the three phases is 7 days long. A specific regimen discloses 20–50 μg EE in combination with 500 μg LNg, 750 μg LNg, and 1 mg LNg during each of the three 7-day phases, respectively.

Edgren (U.S. Pat. No. 4,390,531) discloses triphasic 21-day progestin/estrogen combination regimens in which a dose of 20–40 μg EE (or another estrogen in an equivalent dosage) is administered in all three phases in combination with 0.3–0.8 mg NE (or another progestin in an equivalent dosage) for 5–8 days in the first phase, twice the dose of NE for 7–11 days in the second phase, and the dose of NE being the same as in the first phase for 3–7 days in the third phase. It is preferred that each of the three phases is 7 days. Placebo is administered for 6–8 days following administration of the contraceptive steroid combination. A specific regimen discloses a first phase of 7 days of 0.5 mg NE in combination with 35 μg EE, a second 7 day phase of 1.0 mg NE in combination with 35 μg EE, and a third 7 day phase of 0.5 mg NE in combination with 35 μg EE.

DESCRIPTION OF THE INVENTION

This invention provides a bridged triphasic combination progestin/estrogen oral contraceptive regimen for females of child-bearing age that provides effective contraception, good cycle control, and minimal side effects while greatly reducing the total contraceptive steroid administered (particularly the estrogenic component) per 28-day cycle. To achieve the substantial reduction in the total contraceptive steroid administered per cycle, the low dose progestin/estrogen combination is administered for 23–25-days per cycle according to a triphasic regimen that is described below. Administration of the contraceptive progestin/estrogen combination is begun on the first day of menses (day 1), and continued for 23–25 consecutive days. Following the 23–25-day administration period, an estrogen is administered for 3–5 days to assist in maintaining good cycle control. The total administration during each cycle is 28 days.

More particularly, this invention provides a method of contraception which comprises administering to a female of child bearing age a first phase of a combination of a progestin at a daily dosage of 40–500 μg trimegestone, 250 μg—4 mg dienogest, or 250 μg—4 mg drospirenone, and an estrogen at a daily dosage equivalent in estrogenic activity to 10–20 μg ethinyl estradiol for 3–8 days beginning on day 1 of the menstrual cycle. The same daily dosage of the progestin and estrogen is administered for each of the 3–8 days. A second phase of a combination of a progestin at a daily dosage of 40–500 μg trimegestone, 250 μg—4 mg dienogest, or 250 μg—4 mg drospirenone, and an estrogen at a daily dosage equivalent in estrogenic activity to 10–20 μg ethinyl estradiol is administered for 4–15 days beginning on the day immediately following the last day of administration of the first phase. The same daily dosage of the progestin and estrogen is administered for each of the 4–15 days. A third phase of a combination of a progestin at a daily dosage of 40–500 μg trimegestone, 250 μg—4 mg dienogest, or 250 μg—4 mg drospirenone, and an estrogen at a daily dosage equivalent in estrogenic activity to 10–20 μg ethinyl estradiol at a daily dosage equivalent in estrogenic activity to 10–20 μg ethinyl estradiol is administered for 4–15 days beginning on the day immediately following the last day of administration of the second phase. The same daily dosage of the progestin and estrogen is administered for each of the 4–15 days. The total administration for all three phases is 23–25 days. The daily dosage of the progestin/estrogen combination administered in any phase is distinct from the dosage of the progestin/estrogen combination administered in either of the other two phases.

Following the 23–25-day period, an estrogen phase is administered in which an estrogen at a daily dosage equivalent to 5–20 μg ethinyl estradiol is administered for 3–5 days. The total administration during each cycle is 28 days.

It is preferred that total administration of the progestin/estrogen combination be 24 days. Preferred phase lengths are shown in the following table, with Phase Regimens A and B being most preferred for the bridged triphasic rising regimens that are described below, and Phase Regimens E and F are most preferred for the bridged triphasic midpeak regimens that are described below.

| Phase Regimen | Phase 1 (days) | Phase 2 (days) | Phase 3 (days) | Estrogen Phase (days) |
|---|---|---|---|---|
| A | 7 | 7 | 10 | 4 |
| B | 5 | 5 | 14 | 4 |
| C | 5 | 8 | 11 | 4 |
| D | 6 | 6 | 12 | 4 |
| E | 7 | 10 | 7 | 4 |
| F | 6 | 12 | 6 | 4 |

| Phase Regimen | Phase 1 (days) | Phase 2 (days) | Phase 3 (days) | Estrogen Phase (days) |
|---|---|---|---|---|
| G | 6 | 8 | 10 | 4 |
| H | 4 | 8 | 12 | 4 |
| I | 5 | 14 | 5 | 4 |
| J | 6 | 10 | 8 | 4 |

Preferred estrogens include, but are not limited to ethinyl estradiol; 17β-estradiol; conjugated estrogens, USP; estrone or a salt thereof; and mestranol; with ethinyl estradiol being more preferred. Preferred salts of estrone include, but are not limited to the sodium and piperate salt. When conjugated estrogens, USP are used as the estrogen, it is preferred that the daily dosage is 0.3–5 mg, with a daily dose of 1.25 mg conjugated estrogens, USP being equivalent to a daily dose of 15 μg ethinyl estradiol.

In one specific preferred embodiment of this invention termed a "triphasic rising regimen," the dosage of progestin is higher in the second phase than in the first phase and is higher in the third phase than in the second phase. With these regimens, the third phase will generally have the longest duration. In general, the estrogen dosage in the second phase is greater than the first phase, and the estrogen dosage in third phase is greater than the second phase; can rise from the first phase to the second phase, and then remain the same for the third phase; or can remain the same for all three phases.

The following daily dosages of a combination of trimegestone and ethinyl estradiol are preferred for contraception when administered according to a triphasic rising regimen for 23–25 consecutive days beginning on the first day of menses, with 24 days being preferred. In these regimens, it is preferred that ethinyl estradiol is administered during the estrogen phase for 3–5 days, with 4 days being more preferred, so that the total administration per cycle is 28 days. The preferred phase lengths are provided above. Of the regimens provided below, Regimen B is more preferred. In the table below, trimegestone is abbreviated as TMG and ethinyl estradiol is abbreviated as EE.

PREPERRED DAILY DOSAGES (in μg)

| Regimen | Phase 1 TMG | EE | Phase 2 TMG | EE | Phase 3 TMG | EE | Estrogen Phase EE |
|---|---|---|---|---|---|---|---|
| A | 75 | 10 | 125 | 15 | 250 | 20 | 20 |
| B | 50 | 10 | 75 | 15 | 125 | 20 | 20 |
| C | 40 | 10 | 50 | 15 | 75 | 20 | 20 |
| D | 50 | 10 | 75 | 15 | 125 | 15 | 15 |
| E | 50 | 10 | 75 | 10 | 125 | 15 | 15 |

The following daily dosages of a combination of dienogest and ethinyl estradiol are preferred for contraception when administered according to a triphasic rising regimen for 23–25 consecutive days beginning on the first day of menses, with 24 days being preferred. In these regimens, it is preferred that ethinyl estradiol is administered during the estrogen phase for 3–5 days, with 4 days being more preferred, so that the total administration per cycle is 28 days. The preferred phase lengths are provided above. Of the regimens provided below, Regimen B is more preferred. In the table below, dienogest is abbreviated as DGST and ethinyl estradiol is abbreviated as EE.

PREFERRED DAILY DOSAGES

| Regimen | Phase 1 DGST | EE | Phase 2 DGST | EE | Phase 3 DGST | EE | Estrogen Phase EE |
|---|---|---|---|---|---|---|---|
| A | 750 μg | 10 μg | 1 μg | 15 μg | 2 mg | 20 μg | 20 μg |
| B | 500 μg | 10 μg | 750 μg | 15 μg | 1 mg | 20 μg | 20 μg |
| C | 750 μg | 10 μg | 1 μg | 15 μg | 2 mg | 15 μg | 15 μg |
| D | 500 μg | 10 μg | 750 μg | 15 μg | 1 mg | 15 μg | 15 μg |

The following daily dosages of a combination of drospirenone and ethinyl estradiol are preferred for contraception when administered according to a triphasic rising regimen for 23–25 consecutive days beginning on the first day of menses, with 24 days being preferred. In these regimens, it is preferred that ethinyl estradiol is administered during the estrogen phase for 3–5 days, with 4 days being more preferred, that the total administration per cycle is 28 days. The preferred phase lengths are provided above. Of the regimens provided below, Regimen B is more preferred. In e table below, drospirenone is abbreviated as DRSP and ethinyl estradiol is breviated as EE.

PREFERRED DAILY DOSAGES

| Regimen | Phase 1 DRSP | EE | Phase 2 DRSP | EE | Phase 3 DRSP | EE | Estrogen Phase EE |
|---|---|---|---|---|---|---|---|
| A | 2 mg | 10 μg | 3 mg | 15 μg | 4 mg | 20 μg | 20 μg |
| B | 1 mg | 10 μg | 2 mg | 15 μg | 3 mg | 20 μg | 20 μg |
| C | 500 μg | 10 μg | 1 mg | 15 μg | 2 mg | 20 μg | 20 μg |
| D | 2 mg | 10 μg | 3 mg | 15 μg | 4 mg | 15 μg | 15 μg |
| E | 1 mg | 10 μg | 2 mg | 15 μg | 3 mg | 15 μg | 15 μg |
| F | 500 μg | 10 μg | 1 mg | 15 μg | 2 mg | 15 μg | 15 μg |

In another specific preferred embodiment of this invention termed a "triphasic mid-peak regimen," the dosage of progestin is typically highest in the second phase. The dosage of progestin in the third phase is generally, though not necessarily, higher than in the first phase. With these regimens, the second phase will generally have the longest duration. In general, the estrogen can rise so that the dosage in the second phase is greater than the first phase, and the dosage in third phase is greater than the second phase; can rise from the first phase to the second phase, and then remain the same for the third phase; can remain the same for all three phases; or can be "mid-peak" so that the dose in the second phase is highest, with the dose in the third phase generally being higher than the first phase.

The following daily dosages of a combination of trimegestone and ethinyl estradiol are preferred for contraception when administered according to a triphasic mid-peak regimen for 23–25 consecutive days beginning on the first day of menses, with 24 days being preferred. In these regimens, it is preferred that ethinyl estradiol is administered during the estrogen phase for 3–5 days, with 4 days being more preferred, so that the total administration per cycle is 28 days. The preferred phase lengths are provided above. Of the regimens provided below, Regimen B is more preferred. In, the table below, trimegestone is abbreviated as TMG and ethinyl estradiol is abbreviated as EE.

PREFERRED DAILY DOSAGES (in µg)

| Regimen | Phase 1 | | Phase 2 | | Phase 3 | | Estrogen Phase |
|---|---|---|---|---|---|---|---|
| | TMG | EE | TMG | EE | TMG | EE | EE |
| A | 75 | 10 | 250 | 20 | 125 | 15 | 15 |
| B | 50 | 10 | 125 | 20 | 75 | 15 | 15 |
| C | 40 | 10 | 75 | 20 | 50 | 15 | 15 |
| D | 50 | 10 | 125 | 15 | 75 | 15 | 15 |
| E | 50 | 10 | 125 | 15 | 75 | 10 | 10 |

The following daily dosages of a combination of dienogest and ethinyl estradiol are preferred for contraception when administered according to a triphasic mid-peak regimen for 23–25 consecutive days beginning on the first day of menses, with 24 days being preferred. In these regimens, it is preferred that ethinyl estradiol is administered during the estrogen phase for 3–5 days, with 4 days being more preferred, so that the total administration per cycle is 28 days. The preferred phase lengths are provided above. Of the regimens provided below, Regimen B is more preferred. In the table below, dienogest is abbreviated as DGST and ethinyl estradiol is abbreviated as EE.

PREFERRED DAILY DOSAGES

| Regimen | Phase 1 | | Phase 2 | | Phase 3 | | Estrogen Phase |
|---|---|---|---|---|---|---|---|
| | DGST | EE | DGST | EE | DGST | EE | EE |
| A | 750 µg | 10 µg | 2 mg | 20 µg | 1 mg | 15 µg | 15 µg |
| B | 500 µg | 10 µg | 1 mg | 20 µg | 750 µg | 15 µg | 15 µg |
| C | 750 µg | 10 µg | 2 mg | 15 µg | 1 mg | 15 µg | 15 µg |
| D | 500 µg | 10 µg | 1 mg | 15 µg | 750 µg | 15 µg | 15 µg |

The following daily dosages of a combination of drospirenone and ethinyl estradiol are preferred for contraception when administered according to a triphasic mid-peak regimen for 23–25 consecutive days beginning on the first day of menses, with 24 days being preferred. In these regimens, it is preferred that ethinyl estradiol is administered during the estrogen phase for 3–5 days, with 4 days being more preferred, so that the total administration per cycle is 28 days. The preferred phase lengths are provided above. Of the regimens provided below, Regimen B is more preferred. In the table below, drospirenone is abbreviated as DRSP and ethinyl estradiol is abbreviated as EE.

PREFERRED DAILY DOSAGES

| Regimen | Phase 1 | | Phase 2 | | Phase 3 | | Estrogen Phase |
|---|---|---|---|---|---|---|---|
| | DRSP | EE | DRSP | EE | DRSP | EE | EE |
| A | 2 mg | 10 µg | 4 mg | 20 µg | 3 mg | 15 µg | 15 µg |
| B | 1 mg | 10 µg | 3 mg | 20 µg | 2 mg | 15 µg | 15 µg |
| C | 500 µg | 10 µg | 2 mg | 20 µg | 1 mg | 15 µg | 15 µg |
| D | 2 mg | 10 µg | 4 mg | 15 µg | 3 mg | 15 µg | 15 µg |
| E | 1 mg | 10 µg | 3 mg | 15 µg | 2 mg | 15 µg | 15 µg |
| F | 500 µg | 10 µg | 2 mg | 15 µg | 1 mg | 15 µg | 15 µg |

It is preferred that the combination progestin/estrogen contraceptive be administered in unit dosage form i.e., tablet or pill, with each unit providing the entire daily dosage. It is preferred that the progestin and estrogen are admixed together in the same dosage unit. Such dosage units can be prepared by conventional methodology that is well known to one skilled in the art. In each dosage unit, the contraceptively active progestin and estrogen are combined with excipients, vehicles, pharmaceutically acceptable carriers, and colorants. For example, the following illustrates an acceptable composition of a contraceptive progestin/estrogen combination of this invention.

EXAMPLE 1

Trimegestone, 125 µg

Ethinyl estradiol, 15 µg

Microcrystaline Cellulose

Lactose, NF, Spray Dried

Polaciillin Potassium, NF

Magnesium Stearate

Opadry Pink

Polyethylene Glycol, 1500, Flakes

Water, Purified, USP

Wax E (Phalma)

For administration during the last 3–5 days of the menstrual cycle, it is preferred that the estrogen be administered in unit dosage form i.e., tablet or pill, with each unit providing the entire daily dosage. Such dosage units can be prepared by conventional methodology that is well known to one skilled in the art. In each dosage unit, the estrogen is combined with excipients, vehicles, pharmaceutically acceptable carriers, and colorants. For example, the following illustrates an acceptable estrogen composition of this invention.

EXAMPLE 2

Ethinyl estradiol, 15 µg

Microcrystaline Cellulose

Lactose, NF, Spray Dried

Polacrillin Potassium, NF

Magnesium Stearate

Opadry Pink

Polyethylene Glycol, 1500, Flakes

Water, Purified, USP

Wax E (Pharma)

This invention also provides a contraceptive kit adapted for daily oral administration which comprises, 3–8 first phase dosage units each containing fixed dosage of a combination of a progestin at a daily dosage of 440–500 µg trimegestone, 250 µg—4 mg dienogest, or 250 µg—4 mg drospirenone, and an estrogen at a daily dosage equivalent in estrogenic activity to 10–20 µg ethinyl estradiol; 4–15 second phase dosage units each containing fixed dosage of a combination of a progestin at a daily dosage of 40–500 ,g trimegestone, 250 µg—4 mg dienogest, or 250 µg—4 mg drospirenone, and an estrogen at a daily dosage equivalent in estrogenic activity to 10–20 µg ethinyl estradiol; 4–15 third phase dosage units each containing fixed dosage of a combination of a progestin at a daily dosage of 40–500 µg trimegestone, 250 µg—4 mg dienogest, or 250 µg—4 mg drospirenone, and an estrogen at a daily dosage equivalent in estrogenic activity to 10–20 µg ethinyl estradiol; and 3–5 estrogen phase dosage units each containing a fixed dosage of an estrogen at a daily dosage equivalent to 5–20 µg ethinyl estradiol, such that the total number of combination dosage units is 28. The daily dosage arrangements are preferably arranged in a blister pack or in a dial pack type tablet dispenser. Specific referred progestins and estrogens and the specifically preferred dosages of each combination dosage unit are described above.

What is claimed is:

1. A method of contraception which comprises administering orally to a female of child bearing age for 23–25 consecutive days, a first phase combination of a progestin at a daily dosage selected from the group consisting of 40–500 μg trimegestone, 250 μg—4 mg dienogest, and 250 μg—4 mg drospirenone, and an estrogen at a daily dosage equivalent in estrogenic activity to 10–20 μg ethinyl estradiol for 3–8 days beginning on day 1 of the menstrual cycle, wherein the same dosage of the progestin and estrogen combination is administered in each of the 3–8 days, a second phase combination of a progestin at a daily dosage selected from the group consisting of 40–500 μg trimegestone, 250 μg—4 mg dienogest, and 250 μg—4 mg drospirenone, and an estrogen at a daily dosage equivalent in estrogenic activity to 10–20 μg ethinyl estradiol, for 4–15 days beginning on the day immediately following the last day of administration of the first phase combination, wherein the same dosage of the progestin and estrogen combination is administered in each of the 4–15 days, a third phase combination of a progestin at a daily dosage selected from the group consisting of 40–500 fig trimegestone, 250 μg—4 mg dienogest, and 250 μg—4 mg μg drospirenone, and an estrogen at a daily dosage equivalent in estrogenic activity to 10–20 μg ethinyl estradiol, for 4–15 days beginning on the day immediately following the last day of administration of the second phase combination, wherein the same dosage of the progestin and estrogen combination is administered in each of the 4–15 days, and an estrogen phase estrogen at a daily dosage equivalent in estrogenic activity to 5–20 μg ethinyl estradiol, for 3–5 days beginning on the day immediately following the last day of administration of the third phase combination, wherein the same dosage of the estrogen is administered in each of the 3–5 days, provided that the daily dosage of the combination administered in the first phase is not the same as the daily dosage of the combination administered in the second phase and that the daily dosage of the combination administered in the second phase is not the same as the daily dosage of the combination administered in the third phase.

2. The method according to claim 1, wherein the estrogen estrogen administered in the first, second, and third phase combinations and in the estrogen phase is selected from the group consisting of ethinyl estradiol; 17β-estradiol; conjugated estrogens, USP; estrone or a salt thereof; and mestranol.

3. The method according to claim 2, wherein the estrogen is ethinyl estradiol.

4. The method according to claim 3, wherein the progestin of the first phase combination is administered at a daily dosage selected from the group consisting of 40–75 μg trimegestone, 500–750 μg dienogest, and 500 μg—2 mg drospirenone, the progestin of the second phase combination is administered at a daily dosage selected from the group consisting of 50–125 μg trimegestone, 750 μg—1 mg dienogest, and 1–3 mg drospirenone, and the progestin of the third phase combination is administered at a daily dosage selected from the group consisting of 75–250 μg trimegestone, 1–2 mg dienogest, and 2–4 mg drospirenone.

5. The method according to claim 4, wherein the total days of administration of the first phase combination plus the second phase combination plus the third phase combination is 24.

6. The method according to claim 5, wherein the first phase combination is administered for 7 days, the second phase combination is administered for 7 days, and the third phase combination is administered for 10 days.

7. The method according to claim 5, wherein the first phase combination is administered for 5 days, the second phase combination is administered for 5 days, and the third phase combination is administered for 14 days.

8. The method according to claim 5, wherein the daily dosage of trimegestone administered in the first phase combination is 50 μg, the daily dosage of trimegestone administered in the second phase combination is 75 μg, the daily dosage of trimegestone administered in the third phase combination is 125 μg, the daily dosage of ethinyl estradiol administered in the first phase combination is 10 μg, the daily dosage of ethinyl estradiol administered in the second phase combination is 15 μg, the daily dosage of ethinyl estradiol administered in the third phase combination is 20 μg, and the daily dosage of ethinyl estradiol administered in the estrogen phase is 20 μg.

9. The method according to claim 5, wherein the daily dosage of dienogest administered in the first phase combination is 500 μg, the daily dosage of dienogest administered in the second phase combination is 750 μg, the daily dosage of dienogest administered in the third phase combination is 1 mg, the daily dosage of ethyl estradiol administered in the first phase combination is 10 μg, the daily dosage of ethinyl estradiol administered in the second phase combination is 15 μg, the daily dosage of ethinyl estradiol administered in the third phase combination is 20 μg, and the daily dosage of ethinyl estradiol administered in the estrogen phase is 20 μg.

10. The method according to claim 5, wherein the daily dosage of drospirenone administered in the first phase combination is 1 mg, the daily dosage of drospirenone administered in the second phase combination is 2 mg, the daily dosage of drospirenone administered in the third phase combination is 3 mg, the daily dosage of ethinyl estradiol administered in the first phase combination is 10 μg, the daily dosage of ethinyl estradiol administered in the second phase combination is 15 μg, the daily dosage of ethinyl estradiol administered in the third phase combination is 20 μg, and the daily dosage of ethinyl estradiol administered in the estrogen phase is 20 μg.

11. The method according to claim 3, wherein the progestin of the first phase combination is administered at a daily dosage selected from the group consisting of 40–75 μg trimegestone, 500–750 μg dienogest, and 500 μg—2 mg drospirenone, the progestin of the second phase combination is administered at a daily dosage selected from the group consisting of 50–125 μg trimegestone, 750 μg—1 mg dienogest, and 1–3 mg drospirenone, and the progestin of the third phase combination is administered at a daily dosage selected from the group consisting of 75–250 μg trimegestone, 1–2 mg dienogest, and 2–4 mg drospirenone.

12. The method according to claim 11, wherein the total days of administration of the first phase combination plus the second phase combination plus the third phase combination is 24.

13. The method according to claim 12, wherein the first phase combination is administered for 7 days, the second phase combination is administered for 10 days, and the third phase combination is administered for 7 days.

14. The method according to claim 12, wherein the first phase combination is administered for 6 days, the second phase combination is administered for 12 days, and the third phase combination is administered for 6 days.

15. The method according to claim 12, wherein the daily dosage of trimegestone administered in the first phase combination is 50 μg, the daily dosage of trimegestone administered in the second phase combination is 125 μg, the daily dosage of trimegestone administered in the third phase combination is 75 μg, the daily dosage of ethinyl estradiol administered in the first phase combination is 10 μg, the daily dosage of ethinyl estradiol administered in the second phase combination is 20 μg, the daily dosage of ethinyl estradiol administered in the third phase combination is 15 μg, and the daily dosage of ethinyl estradiol administered in the estrogen phase is 15 μg.

16. The method according to claim 12, wherein the daily dosage of dienogest administered in the first phase combination is 500 μg, the daily dosage of dienogest administered in the second phase combination is 1 mg, the daily dosage of dienogest administered in the third phase combination is 750 μg, the daily dosage of ethinyl estradiol administered in the first phase combination is 10 μg, the daily dosage of ethinyl estradiol administered in the second phase combination is 20 μg, the daily dosage of ethinyl estradiol administered in the third phase combination is 15 μg, and the daily dosage of ethinyl estradiol administered in the estrogen phase is 15 μg.

17. The method according to claim 12, wherein the daily dosage of drospirenone administered in the first phase combination is 500 μg, the daily dosage of drospirenone administered in the second phase combination is 2 mg, the daily dosage of drospirenone administered in the third phase combination is 1 mg, the daily dosage of ethinyl estradiol administered in the first phase combination is 10 μg, the daily dosage of ethinyl estradiol administered in the second phase combination is 250 μg, the daily dosage of ethinyl estradiol administered in the third phase combination is 250 μg, and the daily dosage of ethinyl estradiol administered in the estrogen phase is 250 μg.

18. A contraceptive kit adapted for daily oral administration which comprises;

3–8 first phase dosage units each containing a combination of a progestin at a daily dosage selected from the group consisting of 40–500 μg trimegestone, 250 μg—4 mg dienogest, and 250 μg—4 mg drospirenone, and an estrogen at a daily dosage equivalent in estrogenic activity to 10–20 μg ethinyl estradiol, provided that each of the dosage units contains the same dosage of progestin and estrogen;

4–15 second phase dosage units each containing a combination of a progestin at a daily dosage selected from the group consisting of 40–500 μg trimegestone, 250 μg—4 mg dienogest, and 250 μg—4 mg drospirenone, and an estrogen at a daily dosage equivalent in estrogenic activity to 10–20 μg ethinyl estradiol, provided that each of the dosage units contains the same dosage of progestin and estrogen, 4–15 third phase dosage units each containing a combination of a progestin at a daily dosage selected from the group consisting of 40–500 μg trimegestone, 250 μg—4 mg dienogest, and 250 μg—4 mg drospirenone, and an estrogen at a daily dosage equivalent in estrogenic activity to 10–20 μg ethinyl estradiol, provided that each of the dosage units contains the same dosage of progestin and estrogen, and 3–5 estrogen phase dosage units each containing an estrogen at a daily dosage equivalent in estrogenic activity to 5–20 μg ethinyl estradiol, provided that each of the dosage units contains the same dosage the estrogen, and provided that the daily dosage of the first phase dosage units are not the same as the daily dosage of the second phase dosage units, and that the daily dosage of the second phase dosage units are not the same as the daily dosage of the third phase dosage units, such that the total number of dosage units in the kit equals 28.

19. The contraceptive kit according to claim 18 wherein the estrogen is the same for all three phases and is selected from the group consisting of ethinyl estradiol; 17β-estradiol; conjugated estrogens, USP; estrone or a salt thereof; and mestranol.

20. The contraceptive kit according to claim 19, wherein the total number of first phase plus second phase plus third phase dosage units equals 24, and the number of estrogen phase dosage units equals 4.

* * * * *